US00PP21493P2

(12) United States Plant Patent
Westhoff

(10) Patent No.: US PP21,493 P2
(45) Date of Patent: Nov. 16, 2010

(54) ***PETUNIA* PLANT NAMED 'BALPERBLUES'**

(50) Latin Name: *Petunia×hybrida*
Varietal Denomination: Balperblues

(76) Inventor: Heinrich Westhoff, Fresenhorst 26, Südlohn (DE) 46351

( * ) Notice: Subject to any disclaimer, the term of this patent is extended or adjusted under 35 U.S.C. 154(b) by 0 days.

(21) Appl. No.: 12/584,022

(22) Filed: Aug. 28, 2009

(51) Int. Cl.
*A01H 5/00* (2006.01)

(52) U.S. Cl. ..... Plt./356

(58) Field of Classification Search ..... Plt./356
See application file for complete search history.

*Primary Examiner*—June Hwu
(74) *Attorney, Agent, or Firm*—Audrey Charles

(57) ABSTRACT

A new and distinct cultivar of *Petunia* plant named 'Balperblues', characterized by its bluish-purple with white margined bicolored flowers, medium green colored-foliage, moderately vigorous, semi-upright growth habit, is disclosed.

1 Drawing Sheet

Latin name of genus and species of plant claimed: *Petunia× hybrida.*

Variety denomination: 'Balperblues'.

BACKGROUND OF THE INVENTION

The present invention relates to a new and distinct cultivar of *Petunia* plant botanically known as *Petunia×hybrida* and hereinafter referred to by the cultivar name 'Balperblues'.

The new cultivar originated in a controlled breeding program in Südlohn, Germany during Summer 2005. The objective of the breeding program was the development of *Petunia* cultivars with single type flowers, unique flower coloration, and semi-upright growth habit.

The new *Petunia* cultivar is the result of cross-pollination. The female (seed) parent of the new cultivar is the proprietary *Petunia* sp breeding selection designated 05P633, not patented, characterized by its medium purple-colored flowers, medium green-colored foliage, and moderately vigorous, trailing growth habit. The male (pollen) parent of the new cultivar is the proprietary *Petunia* sp breeding selection designated 05P413, not patented, characterized by its dark blue with white margined bicolored flowers, medium green-colored foliage, and moderately vigorous, trailing growth habit. The new cultivar was discovered and selected as a single flowering plant within the progeny of the above stated cross-pollination during May 2006 in a controlled environment at Südlohn, Germany.

Asexual reproduction of the new cultivar by terminal stem cuttings since May 2006 at Südlohn, Germany; Arroyo Grande, Calif.; and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balperblues' as a new and distinct cultivar of *Petunia* plant:

1. Bluish-purple with white margined bicolored flowers;
2. Medium green-colored foliage;
3. Moderately vigorous, semi-upright growth habit.

Plants of the new cultivar differ from plants of the female parent primarily in flower color and growth habit, and from plants of the male parent primarily in growth habit.

Of the many commercially available *Petunia* cultivars, the most similar in comparison to the new cultivar is Happy Hanging Evita, not patented. However, in side by side comparisons, plants of the new cultivar differ from plants of Happy Hanging Evita in at least the following characteristics:

1. Plants of the new cultivar have a more semi-upright habit, as measured by plant height and width, than plants of Happy Hanging Evita;
2. Plants of the new cultivar have a petal margin different from plants of Happy Hanging Evita; and
3. Plants of the new cultivar have smaller leaves, as measured by leaf length and width, than plants of Happy Hanging Evita.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balperblues'. The plants were grown in 4.5 inch pots for 11 weeks in a greenhouse at West Chicago, Ill.

DETAILED BOTANICAL DESCRIPTION

Figure 1:
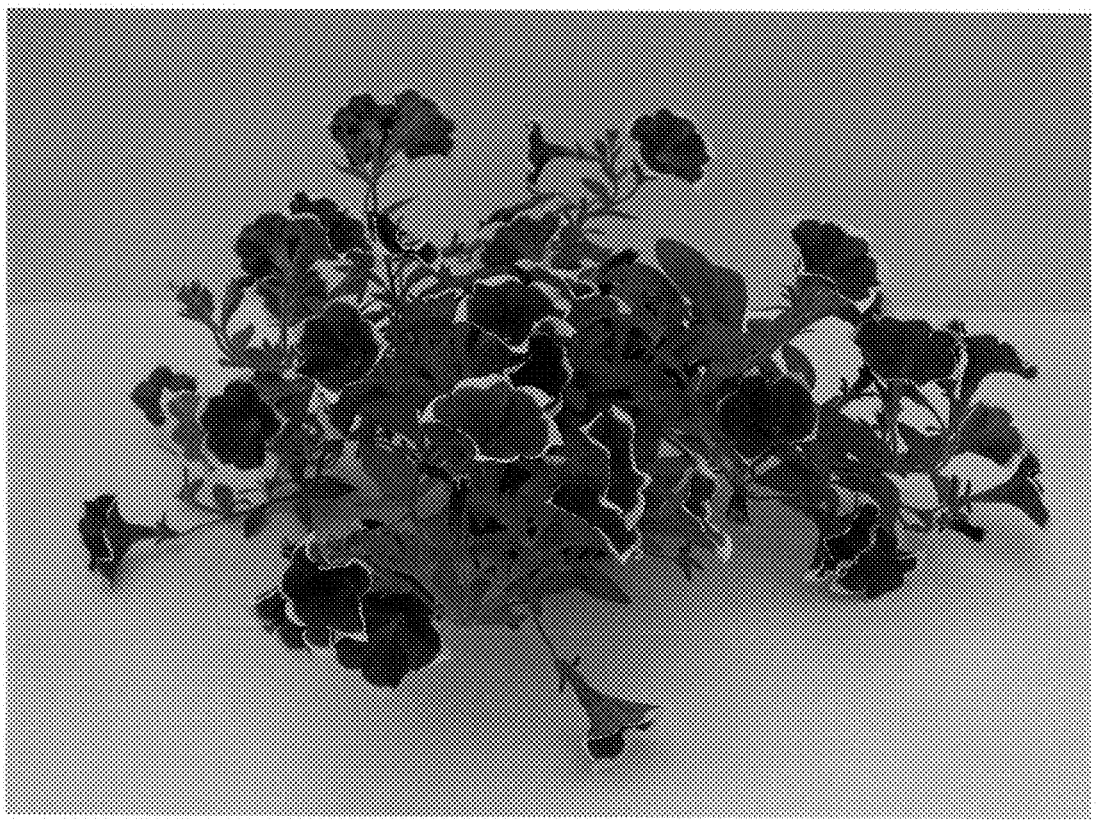
FIG. 1 illustrates a side view of the overall growth and flowering habit of 'Balperblues'.
Figure 2:
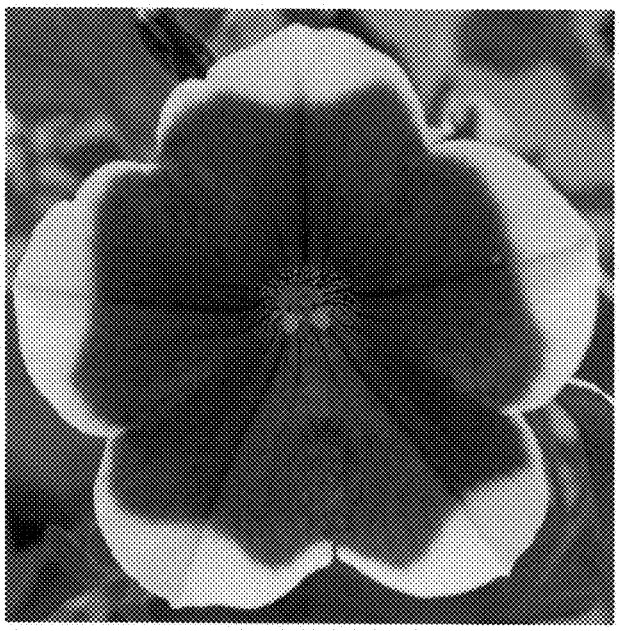
FIG. 2 illustrates a close-up view of an individual flower of 'Balperblues'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined in July 2009 under natural light conditions in West Chicago, Ill.

The following descriptions and measurements describe plants produced from cuttings from stock plants and grown in a glass-covered greenhouse under conditions comparable to those used in commercial practice. The plants were grown at West Chicago, Ill. in 4.5 inch pots for 11 weeks utilizing a soilless growth medium.

Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day. Measurements and numerical values represent averages of typical plants.

Botanical classification: *Petunia×hybrida* cultivar Balperblues.

Parentage:

*Female parent.*—Proprietary *Petunia* sp breeding selection designated 05P633, not patented.

*Male parent.*—Proprietary *Petunia* sp breeding selection designated 05P413, not patented.

Propagation:

*Type cutting.*—Terminal stem.

*Time to initiate roots.*—Approximately 6 to 9 days.

*Time to produce a rooted cutting.*—Approximately 21 to 28 days.

*Root description.*—Fibrous.

*Rooting habit.*—Freely branching.

Plant description:

*Commercial crop time.*—Approximately 6 to 8 weeks from a rooted cutting to finish in a 10 cm pot.

*Growth habit and general appearance.*—Moderately vigorous, semi-upright.

*Size.*—Height from soil level to top of plant plane: Approximately 13.3 cm. Width: Approximately 42.9 cm.

*Branching habit.*—Freely branching, pinching improves basal branching. Quantity of main branches per plant: Approximately 5.

*Branch.*—Strength: Moderate. Length: Approximately 26.9 cm. Diameter: Approximately 3.0 mm. Length of central internode: Approximately 1.9 cm. Texture: Densely glandular pubescent with a mixture of long and short length hairs. Gland color: Colorless. Color of young and mature stems: 144A.

Foliage description:

*General description.*—Quantity of leaves per main branch: Approximately 20. Fragrance: Slight. Form: Simple. Arrangement on flowering stem: Opposite.

*Leaves.*—Aspect: Perpendicular to acute angle to stem. Shape: Ovate. Margin: Entire. Apex: Acute. Base: Attenuate. Venation pattern: Pinnate. Length of mature leaf: Approximately 4.4 cm. Width of mature leaf: Approximately 1.9 cm. Texture of upper and lower surfaces: Moderately glandular pubescent. Gland color: Colorless. Color of upper surface of young foliage: 137C with venation of 144B. Color of lower surface of young and mature foliage: 138B with venation of 144B. Color of upper surface of mature foliage: 137A with venation of 144B.

*Petiole.*—Length: Approximately 5.0 mm. Width: Approximately 2.0 mm. Texture: Densely glandular pubescent with a mixture of long and short length hairs. Gland color: Colorless. Color: 144B.

Flowering description:

*Flowering habit.*—'Balperblues' is freely flowering under outdoor growing conditions with substantially continuous blooming from spring through autumn and year-round in greenhouse environment.

*Lastingness of individual flower on the plant.*—Approximately 10 to 12 days.

Flower description:

*General description.*—Type: Simple, salverform. Quantity per plant: Approximately 33. Fragrance: Slight.

*Bud.*—Rate of opening: Generally takes 2 to 3 days for bud to progress from first color to fully open flower. Quantity per plant: Approximately 10.

*Bud just before opening.*—Shape: Oblong. Length: Approximately 3.4 cm. Diameter at apex: Approximately 6.0 mm. Diameter at base: Approximately 3.0 mm. Texture: Densely glandular pubescent. Gland color: Colorless. Color of petals: 86A with edges of 155D. Color of tube: 86A with venation of N79A.

*Corolla.*—Diameter: Approximately 5.1 cm.

*Petals.*—Quantity: 5, fused to form a tube. Shape: Obovate. Appearance: Velvety. Margin: Entire. Apex: Acute. Length from tube: Approximately 2.4 cm. Length of free portion: Approximately 1.0 cm. Width: Approximately 2.5 cm. Texture of upper surface: Glabrous. Texture of lower surface: Sparsely glandular pubescent. Color of upper surface when first and fully open: Darker than N87A with margins of purer white than 155D. Color of lower surface when first and fully open: 86B with margins of purer white than 155D and midveins of N79A.

*Corolla tube.*—Length: Approximately 2.4 cm. Diameter at distal end: Approximately 7.0 mm. Diameter at proximal end: Approximately 3.0 mm. Texture of inner surface: Glabrous. Texture of outer surface: Densely glandular pubescent. Gland color: Colorless. Color of inner surface: 155A with an overlay of N87A and with venation of N92A. Color of outer surface: 86B with venation of N79A.

*Sepals.*—Quantity per flower: 5, fused at base. Shape: Linear. Apex: Acute. Length: Approximately 1.5 cm. Width: Approximately 3.0 mm. Texture of upper and lower surfaces: Densely glandular pubescent. Color of upper surface: 137A transitioning to 144A at base. Color of lower surface: 137C transitioning to 144A at base.

*Peduncle.*—Strength: Strong. Aspect: Acute angle to stem. Length: Approximately 2.3 cm. Diameter: Approximately 2.0 mm. Texture: Densely glandular pubescent with a mixture of long and short length hairs. Gland color: Colorless. Color: 144A, occasionally have an overlay of 187A at end nearest sepals.

*Reproductive organs.*—Androecium: Stamen quantity: 5, basifixed. Stamen length: Approximately 1.8 cm. Filament length of fixed portion: Approximately 5.0 mm. Filament color: 155D with an overlay of 86A. Anther shape: Bilobed. Anther length: Approximately 1.0 mm. Anther color: 158A. Pollen amount: Abundant. Pollen color: 158D. Gynoecium: Pistil quantity: 1 per flower. Pistil length: Approximately 2.1 cm. Stigma shape: Funnel. Stigma length: Approximately 2.0 mm. Stigma color: 145B. Style length: Approximately 1.7 cm. Style color: 145C. Ovary length: Approximately 2.0 mm. Ovary color: 144A.

Seed and fruit production: Neither seed nor fruit production has been observed.

Disease and pest resistance: Resistance to pathogens and pests common to *Petunia* has not been observed.

What is claimed is:

1. A new and distinct cultivar of *Petunia* plant named 'Balperblues', substantially as herein shown and described.

* * * * *